(12) United States Patent
Thombre et al.

(10) Patent No.: US 6,497,899 B2
(45) Date of Patent: Dec. 24, 2002

(54) RAPIDLY DISINTEGRATING AND FAST-DISSOLVING SOLID DOSAGE FORM

(75) Inventors: Avinash G. Thombre, East Lyme, CT (US); Larry S. Wigman, Swanton, VT (US)

(73) Assignee: Pfizer, Inc., New York, NY (US)

(*) Notice: Subject to any disclaimer, the term of this patent is extended or adjusted under 35 U.S.C. 154(b) by 19 days.

(21) Appl. No.: 09/764,929

(22) Filed: Jan. 18, 2001

(65) Prior Publication Data

US 2002/0034542 A1 Mar. 21, 2002

Related U.S. Application Data

(60) Provisional application No. 60/178,041, filed on Jan. 24, 2000.

(51) Int. Cl.⁷ .................................................. A61K 9/20
(52) U.S. Cl. .................... 424/464; 424/401; 424/484; 424/488
(58) Field of Search ................ 424/401, 464, 424/484, 488

(56) References Cited

U.S. PATENT DOCUMENTS

| | | | |
|---|---|---|---|
| 4,072,535 A | 2/1978 | Short et al. | 106/210 |
| 4,305,502 A | 12/1981 | Gregory et al. | 206/532 |
| 4,371,516 A * | 2/1983 | Gregory et al. | 424/22 |
| 4,863,655 A | 9/1989 | Lacourse et al. | 264/53 |
| 5,035,930 A | 7/1991 | Lacourse et al. | 428/35.6 |
| 5,043,196 A | 8/1991 | Lacourse et al. | 428/35.6 |
| 5,286,769 A | 2/1994 | Eden et al. | 524/49 |
| 5,405,564 A | 4/1995 | Stepto et al. | 264/115 |
| 5,849,233 A * | 12/1998 | Altieri et al. | 264/211.11 |

OTHER PUBLICATIONS

Handbook of Pharmaceutical Excipients, 3ʳᵈ Edition, p. 527 (2000) teaches the non–interchangeability of various starches in pharmaceutical formulations.
United States Pharmacopeia, National Formulary 18, p. 2309 (1995) teaches the non–interchangeability of botanically–derived starches in pharmaceutical formulations.

* cited by examiner

*Primary Examiner*—Jose' G. Dees
*Assistant Examiner*—Konata M. George
(74) *Attorney, Agent, or Firm*—Peter C. Richardson; Gregg C. Benson; Carl J. Goddard

(57) ABSTRACT

Described are non-friable, rapidly disintegrating, fast-dissolving solid dosage forms that are produced from pharmaceutically acceptable steam extruded polymers. The solid dosage forms dissolve in the mouth and are particularly useful for subjects that require or desire oral medication but have difficulty swallowing standard oral dosage forms such as tablets or in subjects suffering from emesis. The solid dosage forms are also useful for rapid drug delivery as vaginal or rectal suppositories or for oral delivery of veterinary drugs.

32 Claims, No Drawings

RAPIDLY DISINTEGRATING AND FAST-DISSOLVING SOLID DOSAGE FORM

CROSS REFERENCE TO RELATED APPLICATIONS

This application claims priority from Provisional Application No. 60/178,041, filed Jan. 24, 2000.

FIELD OF THE INVENTION

This invention relates to highly porous, non-friable, rapidly disintegrating, fast-dissolving solid dosage forms that are produced from pharmaceutically acceptable steam-extruded polymers. The solid dosage forms of the invention dissolve in the mouth and are particularly useful for subjects that require or desire oral medication but have difficulty swallowing standard oral dosage forms such as tablets or in subjects suffering from emesis or who require or desire a faster acting treatment, or a more palatable dosage form. The solid dosage forms of the invention are also useful as vaginal and rectal suppositories.

BACKGROUND OF THE INVENTION

The present invention is a rapidly disintegrating, fast-dissolving dosage form that is broadly applicable for the pediatric, geriatric, HIV-oncology, migraine-CNS, anti-emetic, and animal health therapies. The presently described dosage forms utilize a steam extruded polymeric matrix. Rapidly disintegrating pharmaceutical dosage forms that utilize a non-steam extruded matrix have been described in U.S. Pat. No. 4,371,516 and non-steam extruded, rapidly disintegrating materials related to pharmaceutical dosage forms is described in U.S. Pat. No. 4,305,502.

Steam extruded starch compositions for use in packaging and the methods of producing such compositions have been described in U.S. Pat. Nos. 4,072,535; 4,863,655; 5,035,930; 5,043,196; 5, 286,769; 5,405,564 and 5,849,233.

SUMMARY OF THE INVENTION

This invention relates to rapidly disintegrating, fast-dissolving dosage forms for the delivery of a medicament that are produced from steam extruded pharmaceutically compatible polymers.

A second aspect of the invention is a steam extruded rapidly disintegrating, fast-dissolving dosage form produced from high amylose starch, i.e., one comprising at least about 45% by weight of amylose which is optionally derivatized and optionally comprising about 2% or more by weight of salt.

A third aspect of the invention is a steam extruded rapidly disintegrating, fast-dissolving dosage form produced from gelatin, particularly gelatin that is hydrolyzed, or other polymeric materials such as dextran, dextrin, and alginates (e.g. sodium alginate) or mixtures of polymeric materials with each other or with other carrier materials such as polyvinyl alcohol, polyvinylpyrrolidine or acacia.

A fourth aspect of the invention is a rapidly disintegrating, fast-dissolving dosage form having a uniform, closed cell structure with low density and low friability and good resilience, compressibility, disintegration and dissolution properties. The bulk density of the rapidly disintegrating, fast-dissolving dosage form will be from about 2 to about 80 mg/cc, and preferably from about 2 to about 50 mg/cc; and more preferably from about 2 to about 9 mg/cc excluding medicament and other carriers, vehicles or diluents. The bulk density of the dosage form containing drug will be from about 2 to about 550 mg/cc; and more preferably from about 2 to about 200 mg/cc.

A fifth aspect of the invention is a steam extruded rapidly disintegrating, fast-dissolving dosage form in a shaped configuration for use as a vaginal or rectal suppository.

A sixth aspect of the invention is a method of producing rapidly disintegrating, fast-dissolving dosage forms that involves mixing a medicament with the polymeric material and other optional carriers, vehicles or diluents and steam extruding the medicament-containing polymeric material into an expanded product for forming the dosage form. The medicament-containing extruded polymeric material may be formed into the final dosage form during the steam extrusion process or may undergo subsequent shaping steps such as stamping, cutting, molding or thermoforming.

A seventh aspect of the invention is a method of producing rapidly disintegrating, fast-dissolving dosage forms by steam extruding pharmaceutically acceptable polymeric materials and later loading a medicament into the extrudate. The loading of medicament can take place prior to or subsequent to the final forming or shaping steps such as stamping, cutting, molding or thermoforming.

An eighth aspect of the invention is a method of administering a medicament to a mammal in need thereof by administering a solid dosage form comprising a steam extruded pharmaceutically acceptable polymer and a medicament to the mammal.

A ninth aspect of the invention provides for kits for use by a consumer that require or desire a rapidly disintegrating, fast-dissolving dosage form. The kits comprise a solid dosage form comprising a steam-extruded polymer and a medicament and further comprise a container for holding the dosage form and instructions for the using the dosage form.

A tenth aspect of the invention is a rapidly disintegrating, fast-dissolving veterinary dosage form that is taste-masked so that consumption of the dosage form is desired by an animal thus allowing easy administration of a medicament.

An eleventh aspect of the invention is a rapidly disintegrating, fast-dissolving dosage form containing a drug compound wherein a major portion of the drug is amorphous. As used herein, the term "a major portion" of the drug means that at least 60% of the drug in the dispersion is in the amorphous form, rather than the crystalline form. Preferably, when amorphous drugs are used, the drug added to the rapidly disintegrating, fast-dissolving dosage form is substantially amorphous. As used herein, "substantially amorphous" means that the amount of the drug in crystalline form does not exceed 25% as measured by powder X-ray diffraction analysis or by differential scanning calorimetry or by any other standard quantitative measurement. More preferably, when amorphous drugs are used, the drug added to the rapidly disintegrating, fast-dissolving dosage form is essentially amorphous. As used herein, "essentially amorphous" means that the amount of the drug in crystalline form does not exceed 10% as measured by the methods previously described.

DETAILED DESCRIPTION OF THE INVENTION

The starting materials useful for the rapidly disintegrating, fast-dissolving dosage form must be pharmaceutically acceptable polymeric materials. The polymeric materials used to produce the dosage forms of the invention are highly water-soluble and form a gel phase with hot water under pressure. After extrusion the water rapidly vaporizes leaving a highly porous solid foam. This process is known as "steam extrusion".

A "subject" is an animal including a human that is treatable with the compositions, methods and kits of the present invention. The term "subject" or "subjects" is intended to refer to both the male and female gender unless one gender is specifically indicated.

"Solid dosage form" is defined as a rapidly-disintegrating, fast-dissolving dosage form that can be in the form of granules, pellets, sheets, tablets, capsules, shaped forms and the like.

Amorphous drugs may be used with the rapidly disintegrating, fast-dissolving dosage form to increase the rate of dissolution over crystalline forms of the drugs.

Pharmaceutically acceptable polymers disclosed herein include all manmade and natural polymers and polymeric materials that are compatible with the processes. Non-limiting examples of polymers include gelatin, particularly gelatin that is hydrolyzed, e.g. by heating in water. For example, gelatin may be partially hydrolyzed by heating a solution of the gelatin in water in an autoclave at about 120° C. for up to 2 hours. Other polymeric materials may include dextran, dextrin, alginates (i.e., sodium alginate), hydroxypropyl methylcellulose (HPMC) or mixtures of polymeric materials with each other or with other carrier materials such as polyvinyl alcohol, polyvinylpyrrolidine or acacia. A preferred polymeric material of the invention is high amylose starch, i.e., one containing at least 45% by weight of amylose. The starch used is unlike common starch since it is resilient, not brittle. A typical starch useful for making these materials is produced by National Starch and Chemical Company (Belle Mead, N.J.) and sold under the trade name "Hylon VII". This starch is composed of 70% amylose (short chain—no branching) and 30% amylopectin (large branched molecules). The unique low branching nature contributes to the resilient, not brittle properties and is unlike common starch, which is predominately amylopectin (large branched molecules).

It is well known that starch is composed of two fractions, the molecular arrangement of one being linear and the other being branched. The linear fraction of starch is known as amylose and the branched fraction amylopectin. Starches from different sources, e.g., potato, corn, tapioca, rice, etc., are characterized by different relative proportions of the amylose and amylopectin components. Some plant species have been genetically developed and are characterized by a large preponderance of one fraction over the other. For instance, certain varieties of corn which normally contain about 22–28% amylose have been developed which yield starch composed of over 45% amylose. These hybrid varieties have been referred to as high amylose or amylomaize.

High amylose corn hybrids were developed in order to naturally provide starches of high amylose content and have been available commercially since about 1963. Suitable high amylose starches useful herein are any starches with an amylose content of at least about 45% and preferably at least about 65% by weight. While high amylose corn starch has been especially suitable, other starches which are useful include those derived from any plant species which produces or can be made to produce a high amylose content starch, e.g., corn, peas, barley and rice. Additionally, high amylose starch can be obtained by separation or isolation such as the fractionation of a native starch material or by blending isolated amylose with a native starch.

The high amylose starch used in this invention may be unmodified or modified and the term starch as used herein includes both types. By modified it is meant that the starch can be derivatized or modified by typical processes known in the art, e.g., esterification, etherification, oxidation, acid hydrolysis, cross-linking and enzyme conversion. Typically, modified starches include esters, such as the acetate and the half-esters of dicarboxylic acids, particularly the alkenyl-succinic acids; ethers, such as the hydroxyethyl- and hydroxypropyl starches and starches reacted with hydrophobic cationic epoxides; starches oxidized with hypochlorite; starches reacted with cross-linking agents such as phosphorus oxychloride, epichlorohydrin, and phosphate derivatives prepared by reaction with sodium or potassium orthophosphate or tripolyphosphate and combinations thereof. These and other conventional modifications of starch are described in publications such as Starch: *Chemistry and Technology*, Second Edition, edited by Roy L. Whistler et al. Chapter X; Starch Derivatives: Production and Uses by M. W. Rutenberg et al., Academic Press, Inc., 1984.

One modification of the high amylose starches used in this invention that is especially advantageous, is the etherification with alkylene oxides, particularly those containing 2 to 6, preferably 2 to 4, carbon atoms. Ethylene oxide, propylene oxide and butylene oxide are exemplary compounds useful in etherifying the starting starch materials with propylene oxide being especially preferred. Varying amounts of such compounds may be used depending on the desired properties and economics. Generally, up to 15% or more and preferably, up to about 10%, by weight, based on the weight of starch will be used. Extruded starches modified in this manner, show improved expansion, uniformity and resiliency.

Pharmaceutically acceptable additive compounds may also be combined or blended with the polymeric starting materials to improve properties such as strength, flexibility, resiliency, color, etc. Compounds such as polyvinyl alcohol, monoglyceride, and polyethylene vinyl acetate are typical additives which may be used. They are used in any amount provided the extrusion of the starch and the properties of the expanded product are suitable. Typically, up to about 50% by weight of such additives, and preferably up to about 10% by weight, may be used. Additive polymer compounds may be included for forming or stabilizing solid dispersions of amorphous drug compounds. A preferred class of polymers comprises ionizable and nonionizable cellulosic polymers (including those with ether or ester or a mixture of ester/ether substituents and copolymers thereof, including both so-called "enteric" and "non-enteric" polymers); and vinyl polymers and copolymers having substituents of hydroxyl, alkylacyloxy and cyclicamido.

Exemplary ionic cellulosics include carboxymethylcellulose (CMC) and its sodium salt, carboxyethylcellulose (CEC), hydroxyethylmethylcellulose acetate phthalate, hydroxyethylmethylcellulose acetate succinate, hydroxypropylmethylcellulose phthalate (HPMCP), hydroxypropylmethylcellulose succinate, hydroxypropylcellulose acetate phthalate (HPCAP), hydroxypropylcellulose acetate succinate (HPCAS), hydroxypropylmethylcellulose acetate phthalate (HPMCAP), hydroxypropylmethylcellulose acetate succinate (HPMCAS), hydroxypropylmethylcellulose acetate trimellitate (HPMCAT), hydroxypropylmethylcellulose acetate phthalate (HPMCAP), hydroxypropylcellulose butyrate phthalate, carboxymethylethylcellulose and its sodium salt, cellulose acetate phthalate (CAP), methylcellulose acetate phthalate, cellulose acetate trimellitate (CAT), cellulose acetate terephthalate, cellulose acetate isophthalate, cellulose propionate phthalate, cellulose propionate trimellitate, cellulose butyrate trimellitate and mixtures thereof.

Exemplary nonionic cellulosics include methylcellulose (MC), ethyl cellulose (EC), hydroxyethyl cellulose (HEC), hydroxypropylcellulose (HPC), hydroxypropylmethylcellulose (HPMC), hydroxypropylmethylcellulose acetate, hydroxyethylmethylcellulose, hydroxyethylcellulose acetate, hydroxyethylethylcellulose and mixtures thereof.

Exemplary vinyl polymers and copolymers useful as dispersion polymers include methacrylic acid copolymers, aminoalkyl methacrylate copolymers, carboxylic acid functionalized polymethacrylates, and amine-functionalized polymethacrylates, poly (vinyl acetal) diethylaminoacetate, polyvinyl pyrrolidone (PVP), polyvinyl alcohol (PVA), polyvinyl alcohol/polyvinyl acetate (PVA/PVAc) copolymers and mixtures thereof.

Other useful dispersion polymers include polyethylene glycol/polypropylene glycol (PEG/PPG) copolymers, polyethylene/polyvinyl alcohol (PE/PVA) copolymers, dextrin, pullulan, acacia, tragacanth, sodium alginate, propylene glycol alginate, agar powder, gelatin, starch, processed starch, glucomannan, chitosan and mixtures thereof.

Particularly preferred dispersion polymers are PVA, PVP, PVA/PVAc copolymers and cellulosic polymers that are aqueous-soluble over at least a portion of the pH range 1<pH<8, including HPMC, HPMCP, HPMCAS, CAP, CAT and mixtures thereof.

In addition to the above noted polymeric materials, modified starches and additive compounds, a pregelatinized form of the starch starting material may be used, if desired.

When using modified starch compounds, it is advantageous that the modified starch starting material contains about 2% or more by weight of salt as well as the required high amylose content. The salt in the modified starch can either be added to the already prepared starch starting material or it can be residual salt, as determined by ash content, that remains after the preparation of the modified starch, e.g., in the well known method of producing hydroxyalkyl starch ethers using alkaline conditions where salts such as sodium sulfate and sodium chloride are used. The amount of residual salt in the starch can be controlled by the amount of washing after the modified polymeric product is produced. Inclusion of such salt results in a more uniform closed cell structure. The salt used can be any inorganic, water soluble salt or mixtures thereof and more particularly, an alkali metal or alkaline earth metal salt with the sodium salts such as sodium sulfate and sodium chloride being preferred. The amount of salt used will be about 2% or more and preferably about 3% or more by weight based on the weight of the starch. The particularly useful modified starch materials for this embodiment are the etherified materials such as the hydroxyalkyl starches produced by the etherification with alkylene oxides and the esterified materials such as those acetylated with acetic anhydride, with the etherified materials being preferred.

In preparing the solid dosage forms of the invention, an extrusion process, either alone or in combination with other forming operations, may be used depending on the type of final product desired. A pharmaceutically acceptable polymeric starting material is used as feedstock for an extruder. The expanded polymeric product leaving the extruder is typically in a rope or cylindrical form. By varying the size and configuration of the die opening of the extruder, different forms such as sheets of varying thickness and widths, irregular profiles and other shapes may be obtained.

When dosage forms of different shapes and design are desired, other forming operations subsequent to the extrusion operation may be utilized. One such readily adaptable technique involves thermoforming. In this operation, a material is heated to a temperature at which it is pliable or shapable and then forced against a mold by applying vacuum, air or mechanical pressure. After the expanded polymeric product leaves the extruder, it is still quite hot and malleable and therefore well suited for the thermoforming step. Shaped dosage forms such as tablets can be formed by thermoforming an extruded starch sheet. Additionally, dosage forms of increased density and thickness can be obtained by pressing together layers of one or more extruded polymeric sheets.

Other methods of forming the expanded polymeric products may also be used in addition to or in substitution for the extrusion/thermoforming operations discussed above. Such methods include injection molding, blow molding, extrusion-blow molding and stamping, as well as combinations of these and other methods.

One method used in preparing the solid dosage forms of this invention is an extrusion process wherein the starting polymeric material such as high amylose starch is fed into an extruder and conveyed through the apparatus under select conditions. The product emerging from the extruder is an expanded, closed cell, low density material with good resilience, compression, dissolution and disintegration properties and low friability making it particularly suitable for oral dosing where swallowing of a conventional solid dosage form by a subject is difficult or undesirable.

The important property characteristics of the steam extruded solid dosage form of this invention are its relatively low density, as well as its resilience and compressibility. The uniform, closed cell structure of the product with its characteristic tiny bubble formation results in a resilient, non-friable dosage form that is easily loaded with medicament and is rapidly disintegrating and fast dissolving upon administration. The fast-dissolving dosage form gives a pleasant mouth feel in that it quickly dissolves with slight effervescence into a pleasant-tasting syrup. A closed cell structure is defined as one having largely nonconnecting cells, as opposed to open cells which are largely interconnecting or defined as two or more cells interconnected by broken, punctured or missing cell walls. The tiny bubble formation generally results in a small cell size of typically about 100 to about 600 microns.

In order to obtain the expanded, closed cell structure characteristic of the desired dosage form, it is important that the total moisture content of the pharmaceutically acceptable polymeric material feed be at a level of about 25% or less by weight, based on the dry weight of polymeric material. By total moisture or water content is meant both the residual moisture of the material, that is the amount picked up while stored at ambient conditions, and the amount of water fed to the extruder. Typically, a polymeric material such as starch, and particularly high amylose starch, will contain about 9 to about 12% residual moisture. Enough water must be present to allow the material to be processed, mixed and heated to the desired temperatures. While some water may be added to the extruder, only an amount which will bring the total moisture level to about 25% or less can be added. This is believed to be necessary to allow for the desired expansion and cell structure formation in the prepared product. Accordingly, while the total moisture content that is used for carrying out the process may vary somewhat, depending on the actual material used and other process variations, a range of from about 10 to about 25%, preferably from about 13 to about 19% and more preferably from about 14 to about 17% by weight, will generally be suitable. The temperature of the material in the extruder will be increased to reach about 150° C. to about 250° C. This temperature must be maintained in at least the section of the extruder closest to the die and just before the material leaves the extruder. The die is positioned at the point or location at the end of the extruder from which the extruded material emerges or exits the apparatus into the ambient air. Depending on the particular material being processed, as well as other process variations, this temperature can vary somewhat within the noted range and preferably will be from about 160° C. to about 210° C. When modified starch such as the etherified material is used, the temperature used will preferably be from about 160° C. to about 180° C. while the use of unmodified starch will have a preferred temperature of from about 170° C. to about 210° C. in at least the section of the extruder closest to the die. By maintaining these conditions in the extruder, the material upon leaving the die and extruder outlet into the open air, expands and cools to form an expanded, low density product.

The apparatus used in carrying out this process may be any screw-type extruder. While the use of a single- or twin-screw extruder may be used, it is preferred to use a twin-screw extruder. Such extruders will typically have rotating screws in a horizontal cylindrical barrel with an entry port mounted over one end and a shaping die mounted at the discharge end. When twin screws are used, they may be corotating and intermeshing or nonintermeshing. Each screw will comprise a helical flight or threaded section and typically will have a relatively deep feed section followed by a tapered transition section and a comparatively shallow constant-depth meter section. The screws, which are motor driven, generally fit snuggly into the cylinder or barrel to allow mixing, heating and shearing of the material as it passes through the extruder.

Control of the temperature along the length of the extruder barrel is important and is controlled in zones along the length of the screw. Heat exchange means, typically a passage, such as a channel, chamber or bore located in the barrel wall, for circulating a heated media such as oil, or an electrical heater such as calrod or coil type heaters, is often used. Additionally, heat exchange means may also be placed in or along the shaft of the screw device.

Variations in any of the elements used in the extruder may be made as desired in accordance with conventional design practices in the field. A further description of extrusion and typical design variations can be found in *Encyclopedia of Polymer Science and Engineering*, Vol. 6, 1986, pp. 571 to 631. The expanded polymer product may be formed in different shapes by varying the size and configuration of the die opening. The product thus may be obtained in forms such as sheets, tablets, granules or forms intended for vaginal or rectal suppositories thereby extending the type of configuration in which it might be used.

Thermoforming as well as other forming operations which may be used in making the shaped product of this invention are well known in the art. In carrying out a thermoforming operation, typically the equipment would include a heater (if necessary) or means to maintain/control/adjust the temperature of the sheet or article being worked on, a mold, pressure producing means, i.e., air, vacuum or mechanical as well as auxiliary means to hold and transfer the article, and optional means such as cutting, trimming, etc. A description of illustrative thermoforming operations and equipment used therein may be found in *Encyclopedia of Polymer Science and Engineering*, Vol. 13, 1976, pp. 832 to 843. This and other well known forming operations which may be used are further described in the *Encyclopedia of Chemical Technology*, Vol. 18, 1982, pp. 184 to 206.

The medicament contained in the fast-dissolving dosage form of the invention may be added to the polymeric material prior to extrusion. When the medicament is added to the polymeric material prior to extrusion, the medicament is homogeneously blended with the polymeric material (feed material) and the mixture subjected to extrusion as described above. The medicament may be in amorphous form and may be stabilized with other additives or may also be in the form of an amorphous dispersion. The dosage forms of the present invention may incorporate ingredients in addition to the medicament that may also be blended with the polymeric material prior to extrusion. For example the solid dosage form of the present invention may incorporate pharmaceutically acceptable adjuvants. Such adjuvants include, for example, coloring agents, flavoring agents, preservatives (i.e., bacteriostatic agents), and the like. The medicament may be microencapsulated or coated and certain unit operations may be performed on the medicament to control the particle size which is added to the fast-dissolving dosage form. The fast-dissolving dosage form may also be taste masked for the oral delivery of bitter medicaments. In the case of veterinary drugs, the fast-dissolving dosage form may be formulated to possess a desirable taste so that dosing of the animal with medicament may be readily performed.

The solid dosage forms of the present invention may also be produced by first extruding the polymeric material and cutting or molding the extruded material to the desired size and shape and then subsequently adding or "loading" the medicament to the dosage form. The loading of the medicament to the dosage form can be performed by first dissolving the medicament in a solvent, preferably a non-aqueous solvent, and then applying the solvent containing dissolved medicament to the dosage form. The solvent containing dissolved medicament is absorbed into the dosage form or deposited into the dosage form and then evaporated, leaving the medicament in the dosage form. The deposited or loaded medicament may be in amorphous form and may be stabilized with other additives or may also be in the form of an amorphous dispersion. Other pharmaceutically acceptable adjuvants can be similarly applied to the extruded dosage form in solution either prior to or subsequent to the loading of medicament. Alternatively, adjuvants can be added to the polymeric material prior to extrusion and thereby are contained in the extruded, shaped dosage form prior to the loading of medicament. Non-limiting examples of suitable solvents include methanol, ethanol, acetone and ethylacetate as well as mixtures thereof.

The pharmaceutical solid dosage forms of the invention may be employed to administer a wide variety of pharmaceutical substances. In this specification the term "pharmaceutical substances" not only includes medicaments for administration to human and non-human animals but also contraceptives (particularly oral contraceptives). Typical drugs which can be administered by means of this invention include, for example, drugs for treating coronary disorders, e.g., digoxin, dofetilide; antihistamines e.g., cetirizine; oral vaccines; enzymes; anti-anginal drugs, e.g., glyceryl trinitrate; peripheral vasodilators and anti-hypertensives e.g., indoramin amlodipine, nifedipine; vasoconstrictors, e.g., ergotamine; analgesics e.g., meptazinol, pentazocine; hypnotics; major and minor tranquillizers e.g., lorazepam, oxazepam, temazepam; anti-depressants e.g., ciclazindol, sertraline; anti-convulsants e.g., clonazepam; antibiotics e.g., azithromycin, trovafloxacin, sulbactam; antifungals e.g., fluconazole, voriconazole; CNS stimulants e.g., pemoline; drugs for the treatment of Alzheimer's disease e.g., donepezil; drugs for the treatment of urinary incontinence e.g., darifenacin; drugs for the treatment of osteoporosis e.g., droloxifene; muscle relaxants e.g., orphenadrine; aldose reductase inhibitors e.g., zopolrestat, neuromuscular drugs e.g., pyridostigmine; gonadal hormones and oral contraceptives e.g., ethynyl estradiol, norgestrel; corticosteroids e.g., prednisolone; local anaesthetics; antipsychotics e.g., ziprasidone; HGM-CoA reductase inhibitors e.g., atorvasatin; anti-inflammatories e.g., oxaprozin, celecoxib, valdecoxib; drugs acting on the uterus e.g., hyoscine butyl bromide; antiallergics e.g., triprolidine and drugs relieving poisoning; metabolic dysfunction e.g., methysergide and drugs for the treatment of male erectile dysfunction, e.g., sildenifil; drugs for the treatment of diabetes e.g., glipizide; drugs for the treatment of migraine headache e.g., eletriptan, sumatriptan; adrenergic antagonists e.g., doxazosin. The pharmaceutical dosage form is particularly useful for oral administration of drugs. This form of administration can be used for administration of drugs which are normally absorbed via the gastrointestinal tract but is also useful for administration of drugs (e.g. nitroglycerin) via the buccal route since such drugs may be very rapidly absorbed by the use of the present invention.

All references cited herein are incorporated by reference. In the case of a conflict between the cited references and the present text, the present text will be controlling.

In the following examples which are merely illustrative of the various embodiments of this invention, all parts and percentages are given by weight and all temperatures are in degrees Celsius unless otherwise noted.

The following procedures were used to determine the characteristic properties of material being evaluated and as specified throughout the description and claims:

Bulk Density

Bulk density can be measured by different methods. One method is by simple measurement of the dimensions of a steam extruded polymeric product and calculation of the measured product's volume. The sample steam extruded polymeric product is then weighed and the weight of the product is divided by the calculated volume to determine density. Alternatively, and perhaps more precisely, bulk density is measured by the volume replacement method described by M. Hwang and K. Hayakawa in "Bulk Densities of Cookies Undergoing Commercial Baking Processes", Journal of Food Science, Vol. 45, 1980, pp. 1400–1407. Essentially, this involves taking a beaker of known volume, i.e., 500 ml. and determining the weight of small glass beads (diameter 0.15–0.16 mm) needed to fill the beaker thus establishing the density of the glass beads to be established (Eqn. II (below)). The weight of a sample is measured and by measuring the weight of glass beads that were needed to replace the volume of that sample, the density of the sample was calculated using the following equations:

$$d_s = \frac{W_s}{W_{gr}} \times d_g \quad \text{(Eqn. I)}$$

$$d_g = \frac{W_{gb}}{V_b} \quad \text{(Eqn. II)}$$

where
$d_s$=density of sample
$W_s$=weight of sample
$W_{gr}$=weight of glass beads needed to replace volume of sample
$d_g$=density of glass beads
$W_{gb}$=weight of glass beads needed to fill beaker
$V_b$=volume of beaker Resiliency Resiliency (also called rebound resilience or relaxation) refers to the ability of a material to recover to its original shape after it has been deformed by a force. Resiliency can be determined using a texture analyzer such as a Stevens LFRA Texture Analyzer employing a cylindrical probe (TA-6, 0.25" diameter) run at a probe speed of 0.5 mm/sec and a probe distance of 0.1 mm.

Sample extrudates are cut into 1-inch long pieces, placed on the texture analyzer's sample table, and secured with pins. The probe is lowered automatically using the above conditions. After the probe is fully lowered, it is held at that distance for one minute before being released. The force required to initially compress the sample and the force required to compress the sample after one minute is determined. The percent recovery of the sample is determined by dividing the compression force after one minute by the initial compression force and multiplying by 100. A higher percent recovery corresponds to a material having a better resiliency.

Compressibility

The compressibility, i.e., the force necessary to deform a material of a sample is determined using a texture analyzer employing the conditions as noted above in measuring resiliency.

Sample extrudates cut into 1-inch long pieces are placed on the analyzer's sample table and secured with pins. The probe is lowered and raised automatically with the force required to compress the sample being measured in $g/cm^2$. This analysis is repeated two additional times using a fresh piece of sample extrudate each time. The average of three measurements is taken as the compressibility value. A high value is attributed to a sample that is relatively hard, i.e., less compressible, while a lower value is attributed to a sample that is easily compressible.

Dosage Form Friability

Dosage form friability is measured by the United States Pharmacopeia/National Formulary (USP/NF) method 1261 (United States Pharmacopeia, Rockville, Md., USA) and is summarized below. Measurement of tablet friability supplements other physical strength measurements, such as tablet crushing strength.

For friability measurements, a drum is used with an internal diameter between 283 and 291 mm and a depth between 36 and 40 mm. The drum is of transparent synthetic polymer with polished internal surfaces, and not subject to static build-up. (An apparatus meeting these specifications is available from laboratory supply houses such as VanKel Industries, Inc., 36 Meridian Road, Edison, N.J. 08820, or from Erweka Instruments, Inc., 56 Quirk Road, Milford, Conn. 06460.). One side of the drum is removable. The tablets are tumbled at each turn of the drum by a curved projection with an inside radius between 75.5 and 85.5 mm that extends from the middle of the drum to the outer wall. The drum is attached to the horizontal axis of a device that rotates at 25(±)1 rpm. Thus, at each turn the tablets roll or slide and fall onto the drum wall or onto each other.

For tablets with a unit mass equal to or less than 650 mg, a sample of whole tablets corresponding to 6.5 g is taken. For tablets with a unit mass of more than 650 mg, a sample of ten whole tablets is taken. The tablets are carefully dedusted prior to testing. The tablet sample is accurately weighed and placed in the drum. The drum is rotated 100 times, and the tablets removed. Any loose dust is removed from the tablets and the tablets are accurately weighed.

Generally, the test is run once. If obviously cracked, cleaved, or broken tablets are present in the tablet sample after tumbling, the sample fails the test. If the results are doubtful or if the weight loss is greater than the targeted value, the test should be repeated twice and the mean of the three tests determined. A maximum weight loss of not more than 1% of the weight of the tablets being tested is considered acceptable for most products. In the case of new formulations, an initial weight loss of 0.8% would be permitted until sufficient packaging data are obtained to extend the limit to a targeted value of 1%.

If tablet size or shape causes irregular tumbling, the drum base is adjusted so that the base forms an angle of about 10 degrees with the bench top and the tablets no longer bind together when lying next to each other, which prevents them from falling freely.

Dosage Form Disintegration

Dosage form disintegration is measured by the United States Pharmacopeia/National Formulary (USP/NF) method 701 (United States Pharmacopeia, Rockville, Md., USA) and is summarized below:

For the purposes of this test, disintegration does not imply complete solution of the unit or even of its active constituent. Complete disintegration is defined as that state in which any residue of the unit, except fragments of insoluble coating or capsule shell, remaining on the screen of the test apparatus is a soft mass having no palpably firm core.

Apparatus

The apparatus consists of a basket-rack assembly, a 1000-mL, low-form beaker, 142 to 148 mm in height and having an outside diameter of 103 to 108 mm for the immersion fluid, a thermostatic arrangement for heating the fluid between 35° C. and 39° C., and a device for raising and lowering the basket in the immersion fluid at a constant frequency rate between 29 and 32 cycles per minute through a distance of not less than 5.3 cm and not more than 5.7 cm. The volume of the fluid in the vessel is such that at the highest point of the upward stroke the wire mesh remains at least 2.5 cm below the surface of the fluid and descends to not less than 2.5 cm from the bottom of the vessel on the downward stroke. The time required for the upward stroke is equal to the time required for the downward stroke, and the change in stroke direction is a smooth transition, rather than an abrupt reversal of motion. The basket-rack assembly moves vertically along its axis. There is no appreciable horizontal motion or movement of the axis from the vertical.

Basket-Rack Assembly

The basket-rack assembly consists of six open-ended transparent tubes, each 7.75±0.25 cm long and having an inside diameter of 20.7 to 23 mm and a wall 1.0 to 2.8 mm thick; the tubes are held in a vertical position by two plastic plates, each 8.8 to 9.2 cm in diameter and 5 to 7 mm in thickness, with six holes, each 22 to 26 mm in diameter, equidistant from the center of the plate and equally spaced from one another. Attached to the under surface of the lower plate is a woven stainless steel wire cloth, which has a plain square weave with 1.8- to 2.2-mm mesh apertures and with a wire diameter of 0.60 to 0.655 mm. The parts of the apparatus are assembled and rigidly held by means of three bolts passing through the two plastic plates. A suitable means is provided to suspend the basket-rack assembly from the raising and lowering device using a point on its axis.

The design of the basket-rack assembly may be varied somewhat provided the specifications for the glass tubes and the screen mesh size are maintained.

Procedure

One dosage form is placed in each of the six tubes of the basket and the apparatus is operated using deionized water maintained at 37±2° C. as the immersion fluid. The duration of operation of the apparatus required for the solid dosage form to form a soft mass is recorded.

Dosage Form Dissolution

Dosage form dissolution is measured by the United States Pharmacopeia/National Formulary (USP/NF) method 711 (United States Pharmacopeia, Rockville, Md., USA) and is summarized below:

Apparatus 1

The assembly consists of the following: a covered vessel made of glass or other inert, transparent material; a motor; a metallic drive shaft; and a cylindrical basket. The vessel is partially immersed in a suitable water bath of any convenient size or placed in a heating jacket. The water bath or heating jacket permits holding the temperature inside the vessel at 37±0.5° C. during the test and keeping the bath fluid in constant, smooth motion. No part of the assembly, including the environment in which the assembly is placed, contributes significant motion, agitation, or vibration beyond that due to the smoothly rotating stirring element. An apparatus that permits observation of the specimen and stirring element during the test is preferable. The vessel is cylindrical, with a hemispherical bottom and with one of the following dimensions and capacities: for a nominal capacity of 1 liter, the height is 160 mm to 210 mm and its inside diameter is 98 mm to 106 mm; for a nominal capacity of 2 liters, the height is 280 mm to 300 mm and its inside diameter is 98 mm to 106 mm; and for a nominal capacity of 4 liters, the height is 280 mm to 300 mm and its inside diameter is 145 mm to 155 mm. Its sides are flanged at the top. A fitted cover may be used to retard evaporation. The shaft is positioned so that its axis is not more than 2 mm at any point from the vertical axis of the vessel and rotates smoothly and without significant wobble. A speed-regulating device is used that allows the shaft rotation speed to be selected and maintained at the rate specified in the individual monograph, within ±4%.

The shaft and basket components of the stirring element are fabricated of stainless steel, type 316 or equivalent, to the specifications described in USP/NF method 711. A basket having a gold coating 0.0001 inch (2.5 $\mu$m) thick may be used. The dosage unit is placed in a dry basket at the beginning of each test. The distance between the inside bottom of the vessel and the basket is maintained at 25±2 mm during the test.

Apparatus 2

The assembly from Apparatus 1 is used except that a paddle formed from a blade and a shaft is used as the stirring element. The shaft is positioned so that its axis is not more than 2 mm at any point from the vertical axis of the vessel and rotates smoothly without significant wobble. The vertical center line of the blade passes through the axis of the shaft so that the bottom of the blade is flush with the bottom of the shaft. The distance of 25±2 mm between the blade and the inside bottom of the vessel is maintained during the test. The metallic or suitably inert, rigid blade and shaft comprise a single entity that may be coated with a suitable inert coating. The dosage unit is allowed to sink to the bottom of the vessel before rotation of the blade is started. A small, loose piece of nonreactive material such as not more than a few turns of wire helix may be attached to dosage units that would otherwise float. Other validated sinker devices may be used.

Dissolution Medium

Deionized water is used as the dissolution medium.

Procedure

The stated volume of the dissolution medium (±1%) is placed in the vessel of the apparatus. The dissolution medium is equilibrated to 37±0.5°C., and the thermometer removed. One solid dosage form is placed in the apparatus, taking care to exclude air bubbles from the surface of the dosage-form unit and either apparatus is immediately operated at a rate of 50 rpm. The concentration of dissolved drug in dissolution medium is measured over time by ultraviolet spectrophotometer to calculate the dissolution rate.

EXAMPLES

Example 1

Solid Dosage Form Composition and Dimensions

A steam extruded starch based product ("Eco Pak" packaging peanut, CPI Packaging, Inc., Marlboro, N.J., USA) was obtained and the dimensions of the product were measured on ten individual peanuts sampled at random. The dimensions were found to be relatively uniform as shown in Table 1.

TABLE 1

Steam Extruded, Starch-Based Product Dimensions

| Sample | Length (mm) | Diameter (mm) | Weight (g) |
|---|---|---|---|
| 1 | 41 | 19 | 0.2433 |
| 2 | 48 | 19 | 0.2596 |
| 3 | 45 | 21 | 0.2480 |
| 4 | 48 | 19 | 0.2535 |
| 5 | 44 | 19 | 0.2432 |
| Mean | 45 | 19 | 0.2495 |
| % RSD | 6.5 | 4.6 | 2.8 |

Mean Area = 13 cc
Mean density = 0.020 g/cc

Solid dosage forms containing no medicament were produced by cutting the steam extruded starch-based product into 1 cm lengths thus creating a 1 cm ×1.9 cm diameter cylindrical dosage form. The inactive ingredients are primarily steam extruded starch and can be loaded with at least 75 mg of drug substance (for a 1 cm thick ×1.9 cm diameter cylindrical tablet).

Medicament was loaded on the dosage form by pipetting on an aliquot dissolved in 50/50 v/v methanol/ethanol. Steam extruded starch-based products of this type were found to be insoluble and stable in most non-aqueous solvents. The drug substances and levels used to medicate these tablets are given in Table 2 and were designed to emulate dosages of conventional commercial tablets. The range of drugs and levels used demonstrated the broadly applicable nature of this dosage form while highlighting the use for pediatric, geriatric, HIV-oncology and animal health therapies.

TABLE 2

Dosage Form Medicament

| Product | Drug Substance | Level/Tablet | Representative Therapy |
|---|---|---|---|
| Zyrtec | Cetirizine.HCl | 10 mg | Pediatric |
| Aricept | Donepezil.HCl | 10 mg | Geriatric |
| Diflucan | Fluconazole | 50 mg | HIV-Oncology |
| Rimadyl | Carprofen | 75 mg | Animal Health |

Example 2

Dosage Form Friability Testing

The unmedicated dosage forms were tested for friability using USP/NF method 1261 described above and the percentage loss was less than 1%. Thus, the tablets are non-friable.

Example 3

Dosage Form Disintegration Testing

Sample dosage forms were prepared as described in Example 1 and tested for disintegration by USP/NF method 701, as described above. Tested sample dosage forms had a rapid disintegration time of 21 seconds. Disintegration times of sample dosage forms were measured in the mouths of human volunteers and determined to average 4 seconds.

Example 4

Dissolution Testing

The medicated tablets were dissolved according to USP/NF method 711 using apparatus 2 at 50 RPM. Levels of medicament released were determined by UV absorption. The tablets were observed to disintegrate quickly. Dissolution rates were rapid with 61% of the drug releasing after 1 minute and 80% of the drug releasing after 5 minutes on average. The results are given in Table 3.

TABLE 3

Dissolution Rate Data for Medicated Solid Dosage Forms

| Drug Substance | Cetirizine.HCl | Donepezil.HCl | Diflucan | Carprofen |
|---|---|---|---|---|
| 1 minute release | 65.5% | 84.9% | 60.3% | 33.4% |
| 5 minute release | 82.7% | 90.7% | 76.7% | 69.6% |
| 10 minute release | not tested | not tested | not tested | 82.8% |
| 60 minute release | 100.1% | 98.2% | 97.6% | 101.4% |
| Dissolution Media | deionized H$_2$O | deionized H$_2$O | deionized H$_2$O | Simulated Intestinal Fluid without enzyme |

Additional modifications and variations of the invention will be apparent to one of ordinary skill in the art based upon a reading of this description. Such modifications and variations are intended to be encompassed by the claims appended hereto.

What is claimed is:

1. A solid dosage form comprising:
   a) a pharmaceutically acceptable steam extruded polymer, and
   b) a medicament.

2. A solid dosage form according to claim 1 wherein the polymer is selected from the group consisting of starch, gelatin, dextran, dextrin, alginate, hydroxypropyl methylcellulose and mixtures thereof.

3. A solid dosage form according to claim 2 wherein the polymer is starch.

4. A solid dosage form according to claim 3 wherein the starch contains more than about 45% by weight of amylose.

5. A solid dosage form according to claim 2 wherein the polymer is gelatin.

6. A solid dosage form according to claim 5 wherein the gelatin is hydrolyzed gelatin.

7. A solid dosage form according to claim 1 that is in the shape of a tablet or suppository.

8. A solid dosage form according to claim 1 wherein the steam extruded polymer forms a matrix and wherein the matrix has a density of from about 2 to about 80 mg/cc.

9. A solid dosage form according to claim 8 wherein the density of the matrix is from about 2 to about 50 mg/cc.

10. A solid dosage form according to claim 9 wherein the density of the matrix is from about 2 to about 9 mg/cc.

11. A method of administering a medicament to a subject comprising administering to a subject in need thereof, a rapidly disintegrating solid dosage form comprising:
 a) a pharmaceutically acceptable steam extruded polymer, and
 b) a medicament.

12. A method according to 11 wherein the polymer is selected from the group consisting of starch, gelatin, dextran, dextrin, alginate, hydroxypropyl methylcellulose and mixtures thereof.

13. A method according to 12 wherein the polymer is starch.

14. A method according to 13 wherein the starch contains more than about 45% by weight of amylose.

15. A method according to 12 wherein the polymer is gelatin.

16. A method according to 15 wherein the gelatin is hydrolyzed gelatin.

17. A method according to claim 11 wherein the solid dosage form is in the shape of a tablet or suppository.

18. A method according to claim 11 wherein the steam extruded polymer forms a matrix and wherein the matrix has a density of from about 2 to about 80 mg/cc.

19. A method according to claim 18 wherein the density of the matrix is from about 2 to about 50 mg/cc.

20. A method according to claim 19 wherein the density of the matrix is from about 2 to about 9 mg/cc.

21. A solid dosage form according to claim 1 wherein said medicament is amorphous.

22. A method according to claim 11 wherein said medicament is amorphous.

23. A method of producing a solid dosage form comprising the steps of:
 (a) providing a pharmaceutically acceptable polymeric starting material with a moisture content of about 25% by weight or less in an extruder,
 (b) extruding the polymeric starting material under conditions wherein at least some of the moisture is vaporized upon extrusion to form an expanded product,
 (c) shaping the expanded product into a solid dosage form, and
 (d) adding a medicament to the solid dosage form.

24. A method of producing a solid dosage form comprising the steps of:
 (a) providing a pharmaceutically acceptable polymeric starting material with a moisture content of about 25% by weight or less in an extruder,
 (b) adding a medicament to the polymeric starting material,
 (c) extruding the polymeric starting material under conditions wherein at least some of the moisture is vaporized upon extrusion to form an expanded product, and
 (d) shaping the expanded product into a solid dosage form.

25. A method of producing a solid dosage form comprising the steps of:
 (a) providing a pharmaceutically acceptable polymeric starting material with a moisture content of about 25% by weight or less in an extruder,
 (b) extruding the polymeric starting material under conditions wherein at least some of the moisture is vaporized upon extrusion to form an expanded product,
 (c) adding a medicament to the expanded product, and
 (d) shaping the expanded product into a solid dosage form.

26. A method of producing a solid dosage form comprising the steps of:
 (a) providing a pharmaceutically acceptable polymeric starting material with a moisture content of about 25% by weight or less in an extruder, wherein the polymeric starting material comprises gelatin,
 (b) extruding the polymeric starting material under conditions wherein at least some of the moisture is vaporized upon extrusion to form an expanded product,
 (c) shaping the expanded product into a solid dosage form, and
 d) adding a medicament to the solid dosage form.

27. A method of producing a solid dosage form comprising the steps of:
 (a) providing a pharmaceutically acceptable polymeric starting material with a moisture content of about 25% by weight or less in an extruder,
 (b) extruding the polymeric starting material under conditions wherein at least some of the moisture is vaporized upon extrusion to form an expanded product,
 (c) shaping the expanded product into a tablet or suppository solid dosage form.

28. A method of producing a solid dosage form comprising the steps of:
 (a) providing a pharmaceutically acceptable polymeric starting material with a moisture content of about 25% by weight or less in an extruder,
 (b) extruding the polymeric starting material under conditions wherein at least some of the moisture is vaporized upon extrusion to form an expanded product,
 (c) shaping the expanded product into a solid dosage form, and
 (d) adding a medicament to the solid dosage form by depositing the medicament in a solvent onto the dosage form.

29. A method of producing a solid dosage form comprising the steps of:
 (a) providing a pharmaceutically acceptable polymeric starting material with a moisture content of about 25% by weight or less in an extruder,
 (b) extruding the polymeric starting material under conditions wherein at least some of the moisture is vaporized upon extrusion to form an expanded product,
 (c) shaping the expanded product into a solid dosage form,
 (d) adding a medicament to the solid dosage form by depositing the medicament in a solvent onto the dosage form, and
 (e) removing the solvent.

30. A method of producing a solid dosage form comprising the steps of:
 (a) providing a pharmaceutically acceptable polymeric starting material with a moisture content of about 25% by weight or less in an extruder,
 (b) extruding the polymeric starting material under conditions wherein at least some of the moisture is vaporized upon extrusion to form an expanded product,
 c) shaping the expanded product into a solid dosage form, and (d) adding an amorphous medicament to the solid dosage form.

31. A method of producing a solid dosage form comprising the steps of:
(a) providing a pharmaceutically acceptable polymeric starting material with a moisture content of about 25% by weight or less in an extruder,
(b) adding an amorphous medicament to the polymeric starting material,
(c) extruding the polymeric starting material under conditions wherein at least some of the moisture is vaporized upon extrusion to form an expanded product, and
(d) shaping the expanded product into a solid dosage form.

32. A method of producing a solid dosage form comprising the steps of:
(a) providing a pharmaceutically acceptable polymeric starting material with a moisture content of about 25% by weight or less in an extruder,
(b) extruding the polymeric starting material under conditions wherein at least some of the moisture is vaporized upon extrusion to form an expanded product,
(c) adding an amorphous medicament to the expanded product, and
(d) shaping the expanded product into a solid dosage form.

* * * * *